(12) United States Patent
Duval et al.

(10) Patent No.: US 9,448,221 B2
(45) Date of Patent: Sep. 20, 2016

(54) METHOD, SOLVENT FORMULATION AND APPARATUS FOR THE MEASUREMENT OF THE SALT CONTENT IN PETROLEUM FLUIDS

(75) Inventors: Sebastien A. Duval, Dhahran (SA); Simone Less, Dhahran (SA); Veera Venkata R. Tammana, Dhahran (SA); Regis D. Vilagines, Dhahran (SA)

(73) Assignee: SAUDI ARABIAN OIL COMPANY (SA)

( * ) Notice: Subject to any disclaimer, the term of this patent is extended or adjusted under 35 U.S.C. 154(b) by 996 days.

(21) Appl. No.: 13/110,040

(22) Filed: May 18, 2011

(65) Prior Publication Data

US 2012/0293186 A1 Nov. 22, 2012

(51) Int. Cl.
*G01R 27/28* (2006.01)
*G01N 33/28* (2006.01)
*G01N 27/06* (2006.01)

(52) U.S. Cl.
CPC .......... *G01N 33/2823* (2013.01); *G01N 27/06* (2013.01)

(58) Field of Classification Search
CPC ...... G01N 27/06; G01N 27/02; G01N 27/07; G01N 27/045; G01N 27/041; G01N 27/20; G01N 27/04; G01N 27/9046; G01N 33/2888; G01N 33/2823; G01N 33/2858; G01N 33/18; G01R 27/02; G01R 27/22; G01R 27/32; G01R 27/28; G01R 27/26; G01R 27/16; G01R 27/00; G01R 27/025; G01R 17/00; G01R 31/025; G01R 1/30; G01B 7/003; G01B 7/023; G01D 5/202; G01D 18/00
USPC .......... 324/439, 444, 600, 693, 698, 699, 72
See application file for complete search history.

(56) References Cited

U.S. PATENT DOCUMENTS 3,181,058 A * 4/1965 Gulbrandsen .......... G01N 27/06 137/5
3,779,896 A * 12/1973 Woodle ................ C10G 21/003 208/18

(Continued)

FOREIGN PATENT DOCUMENTS

WO 9742493 A1 11/1997
WO WO 2015175960 A1 * 11/2015 ............. G01N 27/07

OTHER PUBLICATIONS

P-600 Salt in Crude Analyzer Brochure, URL: http://www.orbinstruments.com/pdf/p600web-012008.pdf, Jun. 2006, p. 1-4.*

(Continued)

*Primary Examiner* — Patrick Assouad
*Assistant Examiner* — Sean Curtis
(74) *Attorney, Agent, or Firm* — Bracewell LLP; Contance Gall Rhebergen; Brad Y. Chin

(57) ABSTRACT

A method and apparatus for determining the salt concentration of crude oil using a single solvent that allows for improved safety and accuracy. The apparatus can include a pair of electrodes, a solvent storage container, a power source, a temperature sensor, a computer, and a display device. The method includes introducing a volume of the crude oil and a solvent to a mixing zone and mixing them together to form a homogenized mixture. The temperature and conductivity of the homogenized mixture are measured in order to determine the salt concentration of the homogenized mixture, and subsequently, the salt concentration of the crude oil.

25 Claims, 2 Drawing Sheets

(56) References Cited

U.S. PATENT DOCUMENTS

| | | | | |
|---|---|---|---|---|
| 4,057,491 | A * | 11/1977 | Bushnell | C10G 21/28 203/14 |
| 4,069,141 | A * | 1/1978 | Lionetti | C10G 21/003 208/251 R |
| 4,456,564 | A | 6/1984 | Stapp | |
| 4,691,169 | A * | 9/1987 | Baum | G01N 33/1833 324/448 |
| 4,781,819 | A * | 11/1988 | Chirinos | C10G 21/28 208/188 |
| 4,792,412 | A | 12/1988 | Heilweil | |
| 4,822,475 | A * | 4/1989 | McDaniel | C10G 9/00 208/48 AA |
| 4,837,338 | A | 6/1989 | Krupay et al. | |
| 4,915,819 | A * | 4/1990 | Chirinos | C10G 21/28 208/188 |
| 5,156,975 | A * | 10/1992 | Nelson | C10G 9/16 208/48 AA |
| 5,247,994 | A * | 9/1993 | Nenniger | E21B 36/04 166/303 |
| 5,854,820 | A | 12/1998 | Slijkerman et al. | |
| 5,948,242 | A * | 9/1999 | Ohsol | C10G 21/003 208/179 |
| 6,787,505 | B1 | 9/2004 | Maitland et al. | |
| 7,135,870 | B2 * | 11/2006 | Mohajer | G01N 22/00 324/639 |
| 7,906,462 | B2 * | 3/2011 | Mesher | C09K 8/52 166/305.1 |
| 7,972,496 | B2 * | 7/2011 | Tanaka | C08K 5/01 208/19 |
| 8,043,858 | B2 * | 10/2011 | McDaniel | C10G 31/08 208/188 |
| 8,076,950 | B2 * | 12/2011 | Wee | G01N 33/1833 324/722 |
| 8,841,241 | B2 * | 9/2014 | Weerasooriya | C09K 8/584 166/902 |
| 8,980,080 | B2 * | 3/2015 | Koseoglu | C10G 27/00 196/155 |
| 2002/0036158 | A1 * | 3/2002 | Austin | B01D 3/10 208/184 |
| 2003/0211457 | A1 | 11/2003 | Wing et al. | |
| 2004/0257094 | A1 * | 12/2004 | Halalay | G01N 33/2888 324/698 |
| 2005/0264302 | A1 * | 12/2005 | Mohajer | G01N 22/00 324/639 |
| 2010/0015720 | A1 * | 1/2010 | McDaniel | C10G 31/08 436/164 |
| 2010/0025301 | A1 | 2/2010 | Borgna et al. | |
| 2010/0099584 | A1 * | 4/2010 | Mesher | C09K 8/52 507/90 |
| 2011/0089082 | A1 * | 4/2011 | Snawerdt | C10G 29/22 208/187 |
| 2011/0100877 | A1 * | 5/2011 | Snawerdt | C10G 17/02 208/178 |
| 2011/0108481 | A1 * | 5/2011 | Bajpayee | C02F 1/265 210/642 |
| 2011/0120913 | A1 * | 5/2011 | Snawerdt | C10G 17/04 208/252 |
| 2011/0140704 | A1 * | 6/2011 | Son | G01N 27/06 324/441 |
| 2011/0269650 | A1 * | 11/2011 | Hernandez Altamirano | C07D 265/10 507/90 |
| 2012/0181025 | A1 * | 7/2012 | Barnes | C09K 8/584 166/279 |

OTHER PUBLICATIONS

Fortuny et al. "Measuring Salinity in crude oils: Evaluation of methods and an improved procedure" Feb. 22, 2008, pp. 1241-1248.*

Mackay et al., Interfacial Tensions of Oil, Water, Chemical Dispersant Systems, Dept of Chemical Engineering and Applied Chemistry, University of Toronto, The Canadian Journal of Chemical Engineering, vol. 60, Aug. 1982.*

Shakir and Qasim, Mar. 2015, Extraction of Aromatic Hydrocarbons from Lube Oil Using Different Co-Solvent, Iraqi Journal of Chemical and Petroleum Engineering, vol. 16, No. 1, University of Baghdad College of Engineering.*

Fortuny et al., "Measuring salinity in crude oils: Evaluation of methods and an improved procedure", 87(7) Fuel, IPC Sci. and Tech. Press (2008), pp. 1241-1248.

"P-600 Salt in Crude Analyzer Brochure" (Jan. 1, 2008), retrieved from the Internet: http:/www.orbinstruments.co./PDF/P600web-012008.pdf.

ASTM-D-3230-2005 (Jan. 1, 2005), retrieved from the Internet: http://bzwxw.com/soft/UploadSoft/new3/ASTM--D--3230-2005.PDF.

PCT International Search Report and Written Opinion (PCT/US2012/037925), dated Jul. 24, 2012.

Benin, S.D., Klugman, I.Y., Roman'Ko, K.S. and Sokolov, I.L., A Frequency Dielectric Method of Determining Salt Contents on Crude Petroleum and Petroleum Products, Measurement Techniques, 1974, 1589-1592, 17 (10), Plenum Publishing Corporation, New York, NY.

Standard Test Method for Salts in Crude Oil (Electrometric Method), ASTM International, Designation: D3230-09, pp. 1-7, ASTM Int'l, West Conshohocken, PA.

Standard Test Method for Salt in Crude Oils (Potentiometric Method), ASTM International, Designation: D6470-99 (Reapproved 2010), pp. 1-6, ASTM Int'l, West Conshohocken, PA.

* cited by examiner

METHOD, SOLVENT FORMULATION AND APPARATUS FOR THE MEASUREMENT OF THE SALT CONTENT IN PETROLEUM FLUIDS

TECHNICAL FIELD OF THE INVENTION

The present invention relates to a method and apparatus for measuring the salt concentration of a crude oil sample.

BACKGROUND OF THE INVENTION

Currently, salt content measurement in the crude oil production and refining industry follows either the standard reference method ASTM D3230 or ASTM D6470, both of which are incorporated herein by reference. ASTM D6470 is not practical for on-line measurement as it requires extraction steps. ASTM D3230 requires the utilization of a combination of three chemicals: methanol, butanol, and xylene, to reduce the crude oil resistivity to a measurable range for traditional sensors and common instrumentation. However, these solvents are extremely toxic, volatile, and flammable, which makes them particularly difficult to handle in facilities located in hot environments.

The principle of the method outlined in ASTM D3230 is to dilute a crude oil sample in an alcoholic mixture in order to allow for conductivity readings and to compare the readings to reference values. This method can be applied either off-line on a collected sample or on-line. Off-line measurements are susceptible to errors due to unequal gas desorption, which can be attributed to time lag between sampling and measurement and/or variations of the external temperature and/or the crude oil temperature, improper mix of chemicals, measurement errors, and data reporting. On-line measurements avoid manual sampling and prevent some potential errors. However, in high temperature environments, the use of volatile solvents is inadvisable because it can lead to fires, explosions, or intoxication. Another disadvantage of ASTM D3230 is the limitation in solvent quantity stored on site due to flammability concerns and risks of explosion.

Furthermore, xylene, methanol, and butanol must be added in precise proportions, as any minimum alteration in their volumetric ratio, which is even more likely to occur at high temperatures due to their volatile nature, disturbs the homogeneity and causes erroneous measurement readings. This leads to a complicated measurement procedure, thereby introducing potential errors. Moreover, these issues also require bulky equipment with frequent and careful maintenance.

Therefore, it would be beneficial to provide a method and apparatus that avoids the use of the three listed chemicals, and instead uses a single solvent. It would also be beneficial to provide a solvent that is less toxic, and is more stable under hot weather conditions. It would also be beneficial to provide for a method and apparatus that is capable of measuring the salt concentration on-line.

SUMMARY OF THE INVENTION

The present invention is directed to a method and apparatus that provides one or more of these benefits. In one embodiment, the invention provides for a method for determining a salt concentration of crude oil through the steps of feeding a volume of the crude oil to a mixing zone; introducing a volume of a solvent to the mixing zone and mixing such that the crude oil and the solvent form a homogenized mixture; taking a temperature measurement of the homogenized mixture using a temperature sensor; taking a conductivity measurement of the homogenized mixture using a pair of electrodes; determining the salt concentration of the homogenized mixture based on the temperature measurement and the conductivity measurement of the homogenized mixture; and determining the salt concentration of the crude oil based on the salt concentration of the homogenized mixture, the volume of the crude oil, and the volume of the solvent. In one embodiment, the solvent has a normal boiling point that is substantially above ambient air temperature. In one embodiment, the solvent has a boiling point above 140° C., which allows for a relatively low vapor pressure even if ambient air temperature is relatively high, such as 60° C.

In another embodiment, the solvent can consist essentially of a single solvent with no other solvents present in the mixing zone. In another embodiment, the solvent is operable to solubilize both water and the crude oil into a single phase. In one embodiment, the solvent can exhibit a Relative Energy Difference value with crude oil, as defined by Hansen solubility theory, of less than 1. In another embodiment, the solvent can include a single solvent selected from the group consisting of NMP, ethyl alpha-hydroxy propionate, benzonitrile, dipropylene glycol dimethyl ether, 1-cyclohexyl-2 pyrrolidone, 1-octyl-2-pyrrolidone, 1-dodecyl-2-pyrrolidinone, diethyl glycol monobutyl ether, triethylene glycol monobutyl ether, ethylene glycol butyl ether, propylene glycol butyl ether, di(propylene glycol) butyl ether, propylene glycol propyl ether, tripropylene glycol, and diethylene glycol monoethyl ether. In another embodiment, the solvent can consist essentially of a single solvent selected from the group consisting of NMP, ethyl alpha-hydroxy propionate, benzonitrile, dipropylene glycol dimethyl ether, 1-cyclohexyl-2 pyrrolidone, 1-octyl-2-pyrrolidone, 1-dodecyl-2-pyrrolidinone, diethyl glycol monobutyl ether, triethylene glycol monobutyl ether, ethylene glycol butyl ether, propylene glycol butyl ether, di(propylene glycol) butyl ether, propylene glycol propyl ether, tripropylene glycol, and diethylene glycol monoethyl ether.

In another embodiment, the step of determining the salt concentration of the homogenized mixture can further include the steps of obtaining a calibration curve of conductivity as a function of temperature for a known mixture having a known salt concentration and comparing the conductivity of the homogenized mixture against the calibration curve to determine the salt concentration of the homogenized mixture. Certain embodiments of the present invention provide a system to determine the salt concentration given the operational parameters of the homogenized mixture, including temperature and volume of crude oil and solvent and the calibration curve or other similar aspect, such as a look-up table.

In another embodiment, the method is capable of determining salt concentrations of the crude oil in a range from 0 to 50 pounds of salt per thousand barrels (PTB). In another embodiment, the method can be advantageously conducted in an industrial environment that is either on or off-shore. In another embodiment, the solvent does not include an alcohol or xylene. In another embodiment, because the solvent is much less volatile than in methods practiced heretofore, much larger quantities of the solvent may be stored on-site without decreasing overall safety. In another embodiment, the method can include sending a warning signal from the system to an operator if the salt concentration of the crude oil is above a threshold value. In one embodiment, the threshold value is 10 PTB. Examples of warning signals include, without limitation, audible sounds or alarms, blinking lights, vibrations delivered via mobile device such as a pager, phone, or the like, and a display message, which could be displayed on a monitor, pager, phone, or the like.

In another embodiment, the step of taking a temperature measurement of the homogenized mixture using a temperature sensor includes more than one temperature measurement, and the step of taking a conductivity measurement of the homogenized mixture using a pair of electrodes includes more than one conductivity measurement. In another embodiment, the method can include the step of cleaning the pair of electrodes between successive conductivity measurements. In another embodiment, the step of cleaning the pair of electrodes can be accomplished with a fluid. This fluid can be the same as the chosen solvent, or can be a second solvent that is not the same as the chosen solvent. In another embodiment, the fluid can be crude oil, or a combination of the above.

Embodiments of the present invention also provide for an apparatus that is useful for determining the salt concentration of crude oil. In one embodiment, the apparatus can include a pair of electrodes, a solvent storage container, a power source, a temperature sensor, a computer, data stored on a readable medium, a program product, and a display device. In one embodiment, the pair of electrodes is adaptable for insertion into a homogenized mixture container, wherein the homogenized mixture container is operable to hold a homogenized mixture. In one embodiment, the homogenized mixture can include crude oil and a solvent, wherein the crude oil contains salt, and the pair of electrodes is operable to measure the conductivity of the homogenized mixture. In another embodiment, the solvent storage container is used for storing the solvent, and the solvent storage container is in fluid communication with the homogenized mixture container. In another embodiment, the power source is in electronic communication with the pair of electrodes, and the power source helps to provide a voltage, electric potential energy, to the pair of electrodes. The temperature sensor is operable to measure the temperature of the homogenized mixture. The computer includes a signal processing device having non-transitory computer memory. The computer is preferably in electronic communication with the pair of electrodes and the temperature sensor such that the computer is operable to receive measured data from the pair of electrodes and the temperature sensor. In one embodiment, the data stored on a readable medium includes conductivity values, temperature values, and corresponding salt concentrations for a known mixture of crude oil and solvent. In one embodiment, the program product can be stored in the non-transitory computer memory. Preferably, the program product includes instructions executable for (1) comparing the measured data from the pair of electrodes and the temperature probe with the data stored on the readable medium, (2) determining the salt concentration of the homogenized mixture, and (3) determining the salt concentration of the crude oil based upon the relationship of volume of solvent, volume of crude oil and the salt concentration of the homogenized mixture. In one embodiment, the display device can be in electronic communication with the computer. The display device is operable to receive the salt concentration of the homogenized mixture from the program product and display said salt concentration in a readable form.

In another embodiment, the apparatus is useful for detecting the salt concentration of the crude oil in a range from 0 to 50 PTB. In yet another embodiment, the apparatus can be located in an industrial environment. In another embodiment, the apparatus can be located offshore. In another embodiment, the apparatus can also include a warning system that is operable to send a warning signal to the display device if the salt concentration of the crude oil is above a threshold value. In another embodiment, the warning system could also trigger an alarm signal, such as a visual signal and/or an audible signal that could be appreciated by an operator, both on-site or in a remote facility. In one embodiment, the threshold value can be 10 PTB of salt in the crude oil measured.

In another embodiment, the apparatus can further include a flow controlling means that is operable to introduce the crude oil and the single solvent continuously into the homogenized mixture container. In another embodiment, the apparatus can further include one or more flowmeters for measuring the flow of the crude oil and single solvent. In another embodiment, the flow of the crude oil and the single solvent is measured by the one or more flowmeters and controlled by the flow controlling means to ensure that proper flowrates of the crude oil and the single solvent are introduced to the homogenized mixture container.

BRIEF DESCRIPTION OF THE DRAWINGS

These and other features, aspects, and advantages of the present invention will become better understood with regard to the following description, claims, and accompanying drawings. It is to be noted, however, that the drawings illustrate only several embodiments of the invention and are therefore not to be considered limiting of the invention's scope as it can admit to other equally effective embodiments.

DETAILED DESCRIPTION

While the invention will be described in connection with several embodiments, it will be understood that it is not intended to limit the invention to those embodiments. On the contrary, it is intended to cover all the alternatives, modifications and equivalence as may be included within the spirit and scope of the invention defined by the appended claims.

The various embodiments of the present invention provide a stable solvent which advantageously avoids the problems associated with solvents used in ASTM D3230, discussed earlier in the Background section. Since the solvents described herein have an improved stability, repeatability and accuracy of the measurements are improved, as well as improved ability to store larger amounts of the solvents. Additionally, the solvents used in accordance with various embodiments of the present invention are less toxic than those used in ASTM D3230, and therefore, provide reduced health and safety risks.

In certain embodiments of the present invention, the method can be practiced in a continuous mode. Additionally, less equipment can be used with the elimination of a multi-solvent system, thereby providing additional capital expenditure savings. Additionally, as only one single solvent is used at one time in embodiments of the present invention, the logistics and operating expenditures are significantly reduced as compared with the three-solvent system described in ASTM D3230. Furthermore, ASTM D3230 uses two polar solvents, which must be in precise proportions, to disperse the crude oil sample homogeneously in a single phase. Xylene is then added to dissolve any considerable amounts of asphaltene material present. In one embodiment of the present invention, a single solvent is used that is capable of solubilizing both water and hydrocarbons in a single phase. The method as taught in ASTM D3230 used xylene to solubilize the crude oil components. However, xylene is relatively insoluble in water. Likewise, butanol and methanol are soluble in water, but not in oil. However, the alcohols are able to dissolve xylene, along with anything that is already dissolved in the xylene. As such, the solvents taught in ASTM D3230 are not operable to dissolve both oil and water components in their individual capacities. In embodiments of the present invention, however, the solvent is selected such that it has the proper solubility in crude oil and is polar, such that the solvent can bring the crude oil and water into one phase. In one embodiment, the water includes produced water.

Figure 1:
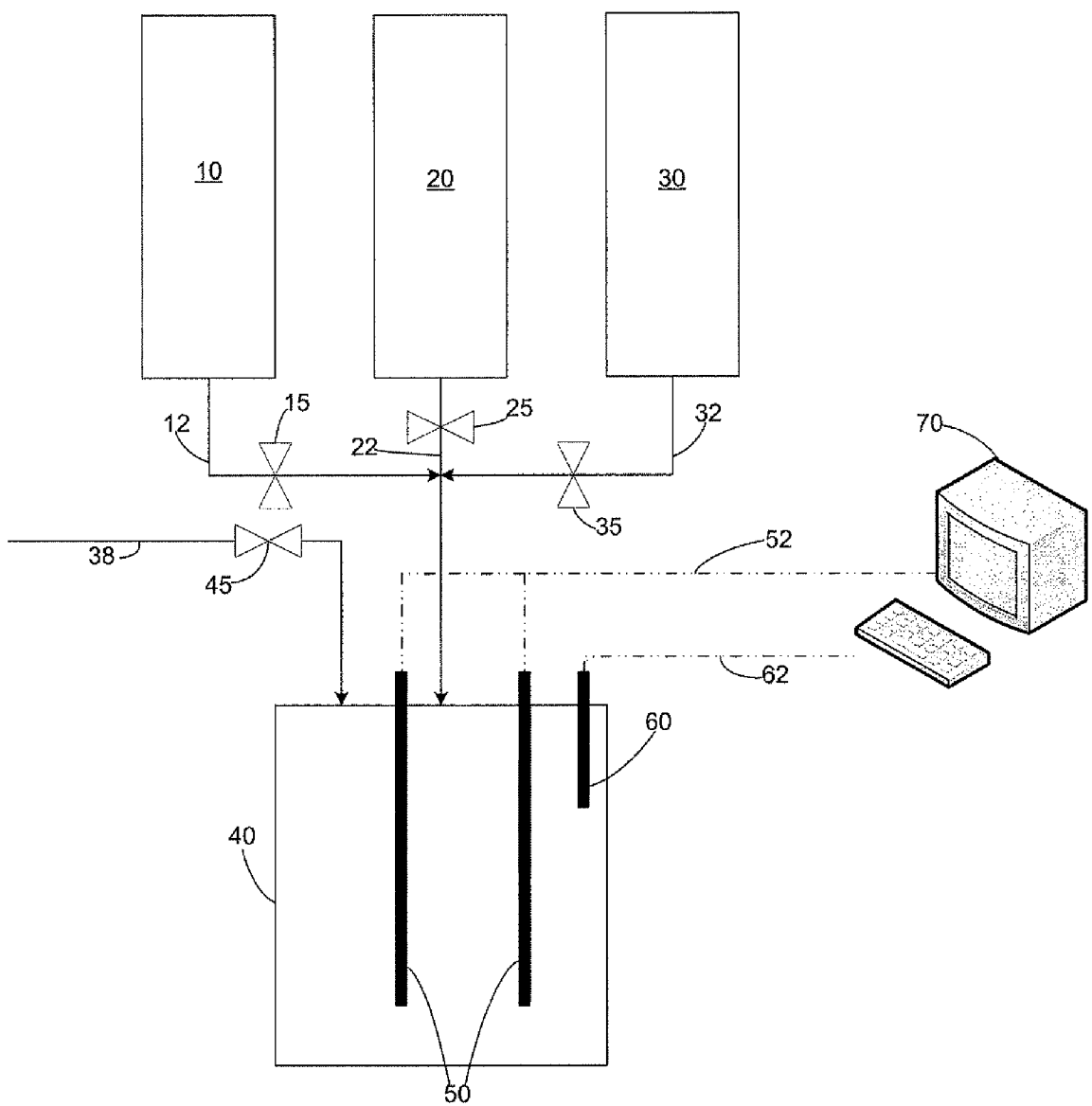
FIG. 1 is a representation of an apparatus for use with the procedures of ASTM-D3230.

FIG. 1 represents a general setup for an apparatus that is in accordance with ASTM D3230. In FIG. 1, there are three storage containers, xylene storage 10, alcohol-mixture storage 20, and naphtha storage 30. The xylene and alcohol-mixture (which includes methanol and butanol) are introduced into homogenized mixture container 40 via lines 12 and 22, respectively. Control valves 15 and 25 are used to help control the flow of each solvent. A precise amount of crude oil sample is introduced into homogenized mixture container 40 via line 38, and is controlled by control valve 45. Once all of the liquids are present, the solution is then mixed to form a homogenized mixture. A pair of electrodes 50 and temperature sensor 60 are inserted into homogenized mixture container. Pair of electrodes 50 and temperature sensor 60 are in communication with computer 70. In ASTM D3230, Naphtha is used to rinse the electrodes following a test. Naphtha is delivered to the pair of electrodes 50 via line 32 by opening control valve 35.

Figure 2:
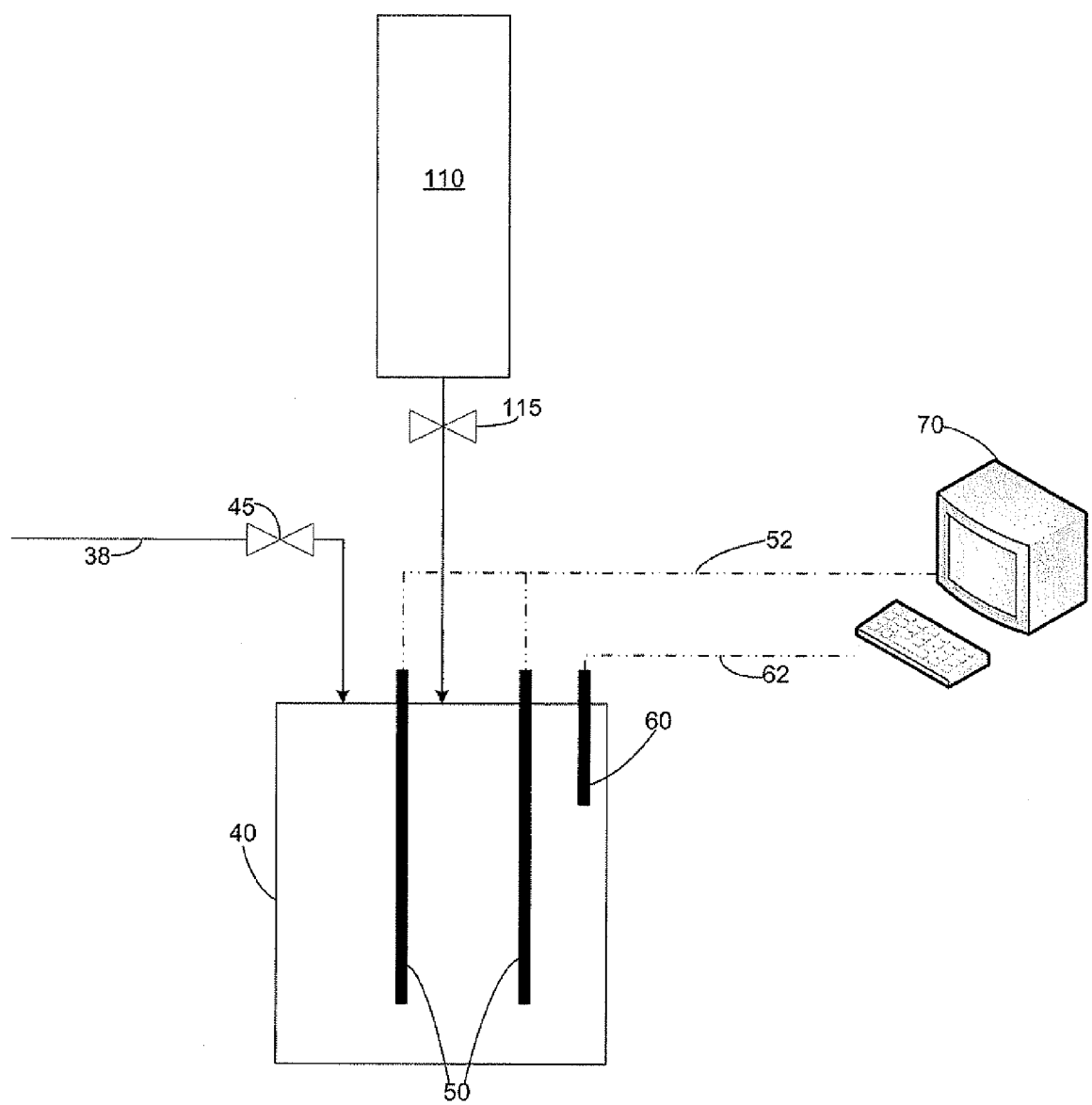
FIG. 2 is a representation of an embodiment of the present invention.

FIG. 2 represents an embodiment of the present invention. In FIG. 2, solvent storage 110 replaces the three storage containers (10, 20, 30) from FIG. 1. Similarly, control valve 115 has replaced the need for the three control valves 15, 25, 35 of the previous set-up. The crude oil sample is introduced into homogenized mixture container 40 via line 38, and is controlled by control valve 45. Once the crude oil and solvent are introduced into homogenized mixture container 40, the solution is then mixed to form a homogenized mixture. A pair of electrodes 50 and temperature sensor 60 are inserted into homogenized mixture container. Pair of electrodes 50 and temperature sensor 60 are in communication with computer 70. Computer 70 contains data that is used to back calculate the salt concentration of the crude oil sample based on the temperature and conductivity measurements taken.

Those of ordinary skill in the art will readily understand that new calibration curves should be made for each solvent used, such that when a conductivity reading and temperature reading are taken, computer 70 can calculate the salt concentration in the crude sample.

Calibration Method

Calibration solutions were prepared in conformance with ASTM D3230 standards. In one embodiment, N-methyl-2-pyrrolidone (NMP) was used as the solvent. 15 mL of NMP was added into a dry, 100-mL graduated, glass-stoppered mixing cylinder. 10 mL of neutral oil was added into the 100-mL graduated cylinder using a 10 mL graduated cylinder. The 10 mL graduated cylinder was rinsed with NMP until free of oil. NMP was added until there was 50 mL of the solution. The mixing cylinder was stoppered and shaken vigorously for approximately 1 minute. In accordance with Table I, a quantity of dilute mixed salts solution was added that is appropriate to the range of salt contents to be measured.

TABLE I

Standard Samples

| Salt (g/m3 of Crude Oil) | Salt (lb/1000 bbl of Crude oil) | Mixed Salts Solution (dilute), mL |
|---|---|---|
| 3 | 1.0 | 0.3 |
| 9 | 3.0 | 1.0 |
| 15 | 5.0 | 1.5 |
| 30 | 10.0 | 3.0 |
| 45 | 16.0 | 4.5 |
| 60 | 21.0 | 6.0 |
| 75 | 26.0 | 8.0 |
| 90 | 31.0 | 9.5 |
| 115 | 40.0 | 12.0 |
| 145 | 51.0 | 15.0 |
| 190 | 66.0 | 20.0 |
| 215 | 75.0 | 22.5 |
| 245 | 86.0 | 25.5 |
| 290 | 101.0 | 30.5 |
| 430 | 151.0 | 45.5 |

The NMP and crude oil mixture was then diluted to 100 mL with additional NMP. Again, the cylinder was shaken vigorously for approximately 30 seconds to effect solution, and then the solution was allowed to stand approximately 5 min. The solution was then poured into a dry test beaker.

A pair of electrodes were quickly placed into the solution in the beaker, making sure that the upper edge of the electrode plates are below the surface of the solution. The voltage was adjusted to a series of values, with the current and voltage being recorded. The electrodes were then removed from the solution, rinsed with NMP, followed by naphtha, and allowed to dry.

The above procedure was repeated using other volumes of mixed salts solution (dilute solution) as needed to cover the range of chloride contents of interest. In order to develop the calibration curve, the value obtained for the blank measurement was subtracted from the indicated current readings of each standard sample.

Experimental Results

In one embodiment, the three solvents were replaced with a single solution of N-methyl-2-pyrrolidone (NMP). The physical properties of NMP are summarized in Table II below:

TABLE II

Physical Properties of NMP

| Boiling Point (760 mmHg) | 204.3° C. |
|---|---|
| Freezing Point (760 mmHg) | −23.6° C. |
| Flash Point (ASTM-D 93-72) | 91° C. |
| Ignition Temperature (ASTM-D 286-58 T) | 270° C. |

Various salt concentrations were created in conformance with the calibration procedure outlined above. Equation 1 below represents an equation of the conductivity as a function of temperature and salt concentration for various mixtures of NMP and crude oil:

$$Conductivity = a + b*SaltConcentration + c*T$$

Additionally, embodiments of the present invention can also increase electrometric measurement accuracy by increasing the fraction of crude in the tested solution, which also results in reducing overall consumption of the solvent.

In one embodiment, the crude content can be increased to 30% by volume of the homogenized mixture, as opposed to the 10% suggested by ASTM 3230.

Similar results as shown above with regards to NMP were found when using the following solvents: ethyl alpha-hydroxy propionate (VERTECBIO EL™), benzonitrile, and dipropylene glycol dimethyl ether (DPGDME). In another embodiment, a non-exhaustive list of solvents that are useful are shown in Table III below.

TABLE III

Non-exhaustive List of Solvents with their Physical Properties

| Solvent Name | Boiling Point (° C.) | Flash Point (° C.) |
|---|---|---|
| 1-Cyclohexyl-2-pyrrolidone | 154 | 141 |
| 1-Octyl-2-pyrrolidone | 171 | 142 |
| 1-Dodecyl-2-pyrrolidinone | 202 | 113 |
| Diethylene glycol monobutyl ether | 225 | 99 |
| Triethylene glycol monobutyl ether | 265-300 | 144 |
| Ethylene glycol butyl ether | 170 | 67 |
| Propylene glycol butyl ether | 170 | 59 |
| Di(propylene glycol) butyl ether, mixture of isomers | 225 | 96 |
| Propylene glycol propyl ether | 140-160 | 48 |
| Tripropylene glycol | 273 | 113 |
| Diethylene glycol monoethyl ether | 202 | 96 |

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed.

We claim:

1. A method for determining a salt concentration of a crude oil, the method comprising the steps of:
    introducing a volume of the crude oil to a mixing zone, the crude oil having salt and water;
    introducing a volume of a solvent to the mixing zone, wherein the solvent has a normal boiling point higher than ambient air temperature and comprises a single solvent that solubilizes both water and the crude oil into a single phase;
    mixing the crude oil and the solvent to form a homogenized mixture;
    taking a temperature measurement of the homogenized mixture using a temperature sensor;
    taking a conductivity measurement of the homogenized mixture using a pair of electrodes;
    determining the salt concentration of the homogenized mixture based on the temperature measurement and the conductivity measurement of the homogenized mixture; and
    determining the salt concentration of the crude oil based on the salt concentration of the homogenized mixture, the volume of the crude oil, and the volume of the solvent,
    wherein the single solvent is selected from the group consisting of NMP, ethyl alpha-hydroxy propionate, benzonitrile, and dipropylene glycol dimethyl ether.

2. The method as claimed in claim 1, wherein the solvent consists of a single solvent.

3. The method as claimed in claim 1, wherein the solvent consists essentially of a single solvent.

4. The method as claimed in claim 1, wherein the solvent has a normal boiling point above 140° C.

5. The method as claimed in claim 1, wherein the solvent has a Relative Energy Difference value with the crude oil of less than 1.0.

6. The method as claimed in claim 1, wherein the step of determining the salt concentration of the homogenized mixture further comprises the steps of:
    obtaining a calibration curve of conductivity as a function of temperature for a known mixture, the known mixture having a known salt concentration; and
    comparing the conductivity of the homogenized mixture against the calibration curve to determine the salt concentration of the homogenized mixture.

7. The method as claimed in claim 1, wherein the method is operable to determine salt concentrations of the crude oil in a range from 0 to 50 pounds of salt per thousand barrels of oil.

8. The method as claimed in claim 1, wherein the method is conducted in an industrial environment.

9. The method as claimed in claim 1, wherein the method is conducted offshore.

10. The method as claimed in claim 1, wherein the solvent comprises an absence of an alcohol or xylene.

11. The method as claimed in claim 1, further comprising sending a warning signal to an operator if the salt concentration of the crude oil is above a threshold value.

12. The method as claimed in claim 11, wherein the threshold value is 10 pounds of salt per thousand barrels of oil.

13. The method as claimed in claim 1, wherein the step of taking a temperature measurement of the homogenized mixture using a temperature sensor includes more than one temperature measurement, wherein the step of taking a conductivity measurement of the homogenized mixture using a pair of electrodes includes more than one conductivity measurement.

14. The method as claimed in claim 13, further comprising the step of cleaning the pair of electrodes between successive conductivity measurements.

15. The method as claimed in claim 14, wherein the step of cleaning the pair of electrodes between successive conductivity measurements comprises washing the pair of electrodes with a fluid, wherein the fluid is selected from the group consisting of the solvent, a second solvent, the crude oil, and combinations thereof wherein the second solvent is not the same as the solvent.

16. An apparatus for determining a salt concentration of crude oil, the apparatus comprising:
    a pair of electrodes adaptable for insertion into a homogenized mixture container, wherein the homogenized mixture container is configured to hold a homogenized mixture, wherein the homogenized mixture comprises crude oil and a solvent, wherein the crude oil contains salt and water, wherein the solvent comprises a single solvent that solubilizes both water and the crude oil into a single phase, and wherein the pair of electrodes are configured to measure the conductivity of the homogenized mixture;
    a solvent storage container for storing the solvent, wherein the solvent storage container is in fluid communication with the homogenized mixture container;
    a power source in electronic communication with the pair of electrodes for providing a voltage to the pair of electrodes;

a temperature sensor for measuring the temperature of the homogenized mixture;

a computer defining a signal processing device having non-transitory computer memory, the computer in electronic communication with the pair of electrodes and the temperature sensor such that the computer is configured to receive measured data from the pair of electrodes and the temperature sensor;

data stored on a readable medium, wherein the data comprises conductivity values, temperature values, and corresponding salt concentrations for a known mixture; and a program product stored in the non-transitory computer memory, the program product composed of instructions executable for:
  (1) comparing the measured data from the pair of electrodes and the temperature sensor with the data stored on the readable medium;
  (2) determining the salt concentration of the homogenized mixture; and
  (3) determining the salt concentration of the crude oil based upon the relationship of volume of solvent, volume of crude oil, and the salt concentration of the homogenized mixture;

a display device in electronic communication with the computer, wherein the display device is configured to receive the salt concentration of the homogenized mixture and the salt concentration of the crude oil mixture from the program product and display said salt concentrations in a readable form, wherein the single solvent is selected from the group consisting of NMP, ethyl alpha-hydroxy propionate, benzonitrile and dipropylene glycol dimethyl ether.

17. The apparatus for determining a salt concentration of crude oil as claimed in claim 16, wherein the apparatus is configured to detect salt concentrations of crude oil in a range from 0 to 50 pounds of salt per thousand barrels of oil.

18. The apparatus for determining a salt concentration of crude oil as in claim 16, wherein the apparatus is located in an industrial environment.

19. The apparatus for determining a salt concentration of crude oil as in claim 16, wherein the apparatus is located offshore.

20. The apparatus for determining a salt concentration of crude oil as claimed in claim 16, further comprising a warning signal that alerts an operator if the salt concentration of the crude oil is above a threshold value.

21. The apparatus for determining a salt concentration of crude oil as claimed in claim 20, wherein the threshold value is 10 pounds of salt per thousand barrels of oil.

22. The apparatus for determining a salt concentration of crude oil as claimed in claim 16, further comprising a flow controlling means that is configured to introduce the crude oil and the solvent continuously into the homogenized mixture container.

23. The apparatus for determining a salt concentration of crude oil as claimed in claim 22, further comprising one or more flowmeters for measuring the flow of the crude oil and solvent.

24. The apparatus for determining a salt concentration of crude oil as claimed in claim 23, wherein the flow of the crude oil and the single solvent is measured by the one or more flowmeters and controlled by the flow controlling means to ensure proper flowrates of the crude oil and the solvent are introduced to the homogenized mixture container.

25. A method for determining a salt concentration of a crude oil, the method comprising the steps of:

introducing a volume of the crude oil to a mixing zone, the crude oil having salt and water;

introducing a volume of a solvent to the mixing zone, wherein the solvent has a normal boiling point higher than ambient air temperature and comprises a single solvent that solubilizes both water and the crude oil into a single phase, wherein the volumetric ratio of the single solvent to the crude oil in the mixing zone is 70%/30%;

mixing the crude oil and the solvent to form a homogenized mixture;

taking a temperature measurement of the homogenized mixture using a temperature sensor;

taking a conductivity measurement of the homogenized mixture using a pair of electrodes;

determining the salt concentration of the homogenized mixture based on the temperature measurement and the conductivity measurement of the homogenized mixture; and determining the salt concentration of the crude oil based on the salt concentration of the homogenized mixture, the volume of the crude oil, and the volume of the solvent.

* * * * *